United States Patent
Chen et al.

(10) Patent No.: US 9,140,623 B2
(45) Date of Patent: Sep. 22, 2015

(54) MEDIA CROSS-SECTIONAL AND AXIAL BEND UNIFORMITY TESTER

(71) Applicant: Verizon Patent and Licensing Inc., Arlington, VA (US)

(72) Inventors: David Zhi Chen, Richardson, TX (US); Mark Anthony Ali, Cockeysville, MD (US)

(73) Assignee: Verizon Patent and Licensing Inc., Basking Ridge, NJ (US)

( * ) Notice: Subject to any disclaimer, the term of this patent is extended or adjusted under 35 U.S.C. 154(b) by 320 days.

(21) Appl. No.: 13/911,735

(22) Filed: Jun. 6, 2013

(65) Prior Publication Data

US 2013/0269455 A1 Oct. 17, 2013

Related U.S. Application Data

(63) Continuation of application No. 12/646,554, filed on Dec. 23, 2009, now Pat. No. 8,468,896.

(51) Int. Cl.
*G01M 11/00* (2006.01)
*G01N 3/20* (2006.01)
*G01M 11/08* (2006.01)

(52) U.S. Cl.
CPC ............ *G01M 11/30* (2013.01); *G01M 11/088* (2013.01); *G01N 3/20* (2013.01); *G01N 2203/028* (2013.01)

(58) Field of Classification Search
USPC ............................................................ 73/849
See application file for complete search history.

(56) References Cited

U.S. PATENT DOCUMENTS

| | | | | | |
|---|---|---|---|---|---|
| 2,435,266 | A | * | 2/1948 | Brillhart | 73/829 |
| 3,643,497 | A | * | 2/1972 | LeCompte | 73/794 |
| 4,286,469 | A | * | 9/1981 | Trias | 73/829 |
| 4,346,601 | A | * | 8/1982 | France | 73/829 |
| 4,947,693 | A | | 8/1990 | Szuchy et al. | |
| 5,016,476 | A | * | 5/1991 | Peterson et al. | 73/829 |
| 5,433,116 | A | | 7/1995 | Ahlstrom et al. | |
| 5,949,935 | A | * | 9/1999 | Schaafsma et al. | 385/43 |
| 2009/0314097 | A1 | | 12/2009 | Cairo et al. | |

* cited by examiner

*Primary Examiner* — Hezron E Williams
*Assistant Examiner* — Mark A Shabman

(57) ABSTRACT

A media tester including a test body having an axial bore configured to receive media having a minimum bend radius, an adjustment member connected to the test body, the adjustment member configured for rotation about the axial bore of the test body, and a media engaging member connected to the adjustment member, the media engaging member configured to receive the media.

22 Claims, 7 Drawing Sheets

MEDIA CROSS-SECTIONAL AND AXIAL BEND UNIFORMITY TESTER

CROSS REFERENCE TO RELATED APPLICATIONS

This application is a continuation of U.S. patent application Ser. No. 12/646,554, filed on Dec. 23, 2009, which is hereby incorporated by reference in its entirety.

BACKGROUND

Bend radius management has become a common requirement when dealing with communication-based media, including cables, wires, and strands. If media is bent such that the minimum bend radius of the media is exceeded, performance may be at least partially compromised. For example, exceeding the minimum bend radius of a fiber optic cable can create attenuations in the cable, where light may escape from the glass core of the cable, resulting in a signal loss. If the fiber optic cable is bent far enough, the transmission of light through the fiber optic cable may stop completely. Under some bending scenarios, the glass core itself could break. Fibers optic cables are typically only tested in one direction or plane to determine if the fiber optic cable meets the optical power loss requirement of a particular minimum bend radius. However, fiber optic cables may be bent in any direction during installation, and at any point along the length of the fiber optic cable. By achieving fiber optic cable cross-sectional and axial power loss uniformity, the required specifications can assist network engineers in determining which fiber optic cables can be used in the FTTX environment based on the application definition and system design criteria.

DETAILED DESCRIPTION

Figure 1:
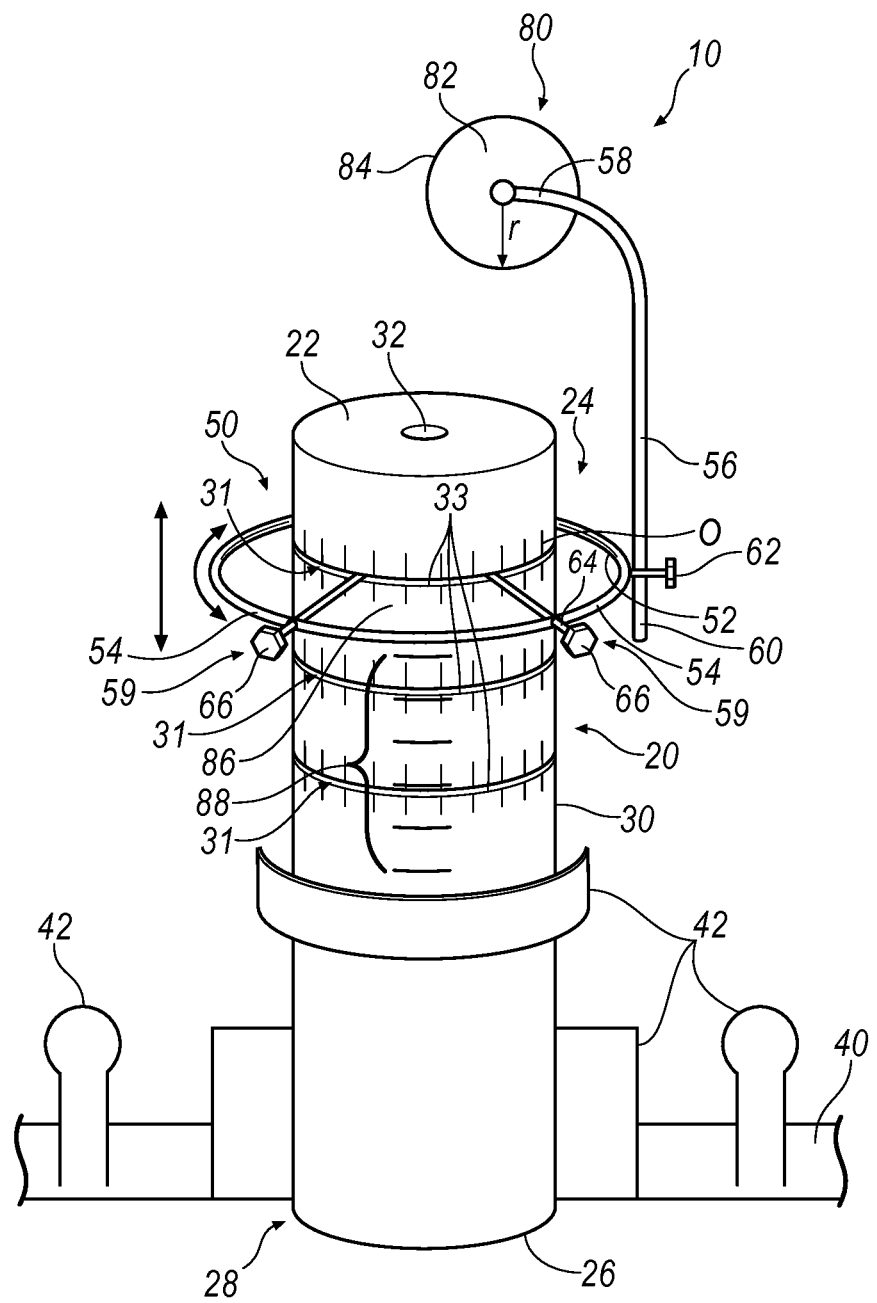
FIG. 1 is a perspective view of a media tester.

Referring now to the discussion that follows and also to the drawings, illustrative approaches to the disclosed apparatuses and methods are shown in detail. Although the drawings represent some possible approaches, the drawings are not necessarily to scale and certain features may be exaggerated, removed, or partially sectioned to better illustrate and explain the disclosed device. Further, the descriptions set forth herein are not intended to be exhaustive or otherwise limit or restrict the claims to the precise forms and configurations shown in the drawings and disclosed in the following detailed description.

Figure 2:
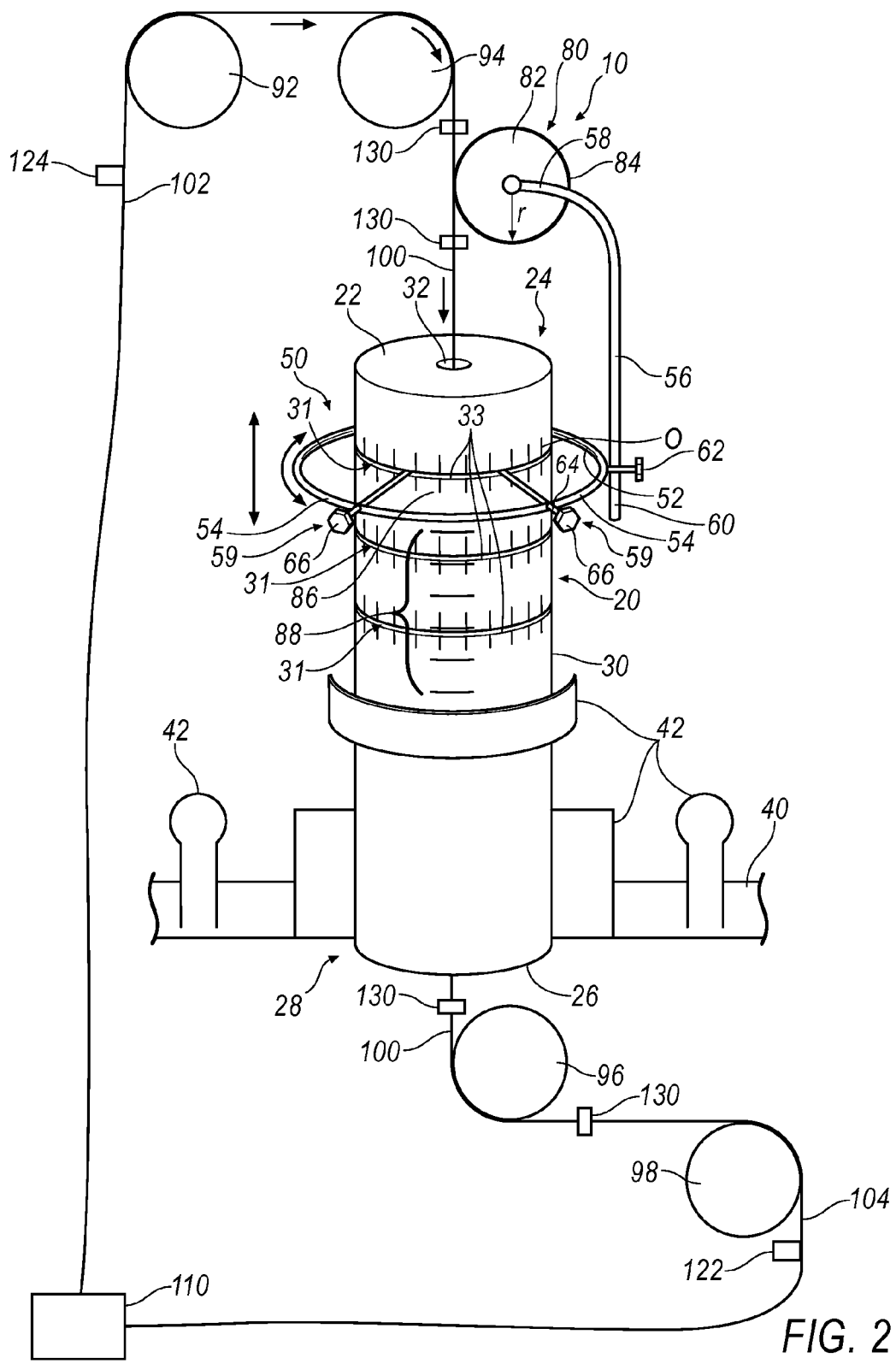
FIG. 2 is a further perspective view of the media tester of FIG. 1.

As seen in FIGS. 1 and 2, an exemplary media tester 10 is configured to test a required bend radius, such as the minimum bend radius, of communications-based media 100, such as fiber optic cables, coaxial cables, wires, or strands. Media tester 10 is configured to test for cross-sectional uniformity and axial uniformity of the required bend radius in media 100. Media tester 10 includes a test body 20, an adjustment member 50 connected to the test body 20, and a media engaging member 80 connected to the adjustment member 50. Media tester 10 receives media 100 having a first end 102 and a second end 104 such that the required bend radius of media 100 can be tested at a plurality of cross-sections of media 100 and at a plurality of locations along the length of media 100.

In the exemplary illustration shown in FIGS. 1 and 2, test body 20 includes an elongated cylinder having a generally circular cross-section. Test body 20 includes a top surface 22 at a first end 24 of the test body 20, a bottom surface 26 at a second end 28 of the test body 20, and an outer surface 30 defined between the top surface 22 and the bottom surface 26. An axial groove 31 having a base surface 33 below the outer surface 30 may be formed in the outer surface 30 about the circumference of test body 20. A plurality of axial grooves 31 may be formed in the outer surface 30. Axial groove 31 may be formed proximate the first end 24 of test body 20. An axial bore 32 extends through test body 20 from the top surface 22 to the bottom surface 26. Axial bore 32 has a diameter slightly larger than the diameter of a media 100 to be tested such that media 100 can pass through test body 20, and the movement of media 100 while inside of test body 20 is limited.

Test body 20 may be mounted to a base 40 to facilitate stabilization of the test body 20 and to limit the movement of the test body during testing of media 100. Base 40 may be provided in a variety of configurations, and any suitable mounting mechanism 42 may be used to mount test body 20 to base 40. Possible mounting mechanisms 42 include, but are not limited to releasable fasteners such as threaded members, clips, clamps and adhesives As seen in FIGS. 1 and 2, media tester 10 may also include an adjustment member 50 connected to the test body 20. In the exemplary illustration, adjustment member 50 includes a generally circular ring having an inner face 52 and an outer face 54, which is disposed about the outer surface 30 of test body 20. Adjustment member 50 may include a bore 64 extending through inner and outer faces 52, 54. Bore 64 is sized and configured (e.g., threaded) as needed to receive a stabilizer 59, such as a stabilizer screw 66. Adjustment member 50 may be aligned with the groove 31 such that the stabilizer screw 66 may pass through bore 64 from the outer surface 54 of the adjustment member 50 and contact the base surface 33 of groove 31. When stabilizer screw 66 is tightened against base surface 33, adjustment member 50 is connected to test body 20 and prevented from moving relative to the test body 20. Adjustment member 50 may include a plurality of stabilizers 59 to secure the adjustment member 50 to the test body 20.

A support arm 56 having a first end 58 and a second end 60 may be connected to the adjustment member 50. The second end 60 of support arm 56 may be connected to either the inner face 52 or outer face 54 of the adjustment member 50. The support arm 56 may be secured to adjustment member 50 by a fastener 62, such as a releasable bolt or screw. The first end 58 of support arm 56 extends above the top surface 22 of test body 20.

As shown in FIGS. 1 and 2, a media engaging member 80 is connected to the first end 58 of support arm 56. Media engaging member 80 may be a drum 82 having a generally circular cross-section and a radius r, and may include a track 84 sized to receive media 100 along the circumference of the drum 82. When a track 84 is used, the track 84 should correspond to the radius r. Support arm 56 and drum 82 may be arranged such that the drum 82 is aligned with and tangential to the axis of the axial bore 32 of test body 20.

The radius r of media engaging member 80 generally corresponds to the required bend radius of the media 100 being tested, such as the minimum bend radius of media 100. For example, if media 100 being tested has a minimum bend radius of 5 millimeters, the radius r of media engaging member 80 is approximately 5 millimeters. Media 100 coiled about the media engagement member 80 will experience a bend that generally corresponds to the radius of media engagement member 80. This allows for the minimum bend radius of media 100 to be tested. Alternatively, media engaging member 80 may have a radius greater than the minimum bend radius of media 100 or a radius less than the minimum bend radius of media 100 to test the durability and performance of the media 100 at other required bend radii.

Media engaging member 80 may be replaced by a further media engaging member 80 having a different radius. To replace media engaging member 80, support arm 56 may be unsecured from adjustment member 50 by removing the fastener 62 from the adjustment member 50. Support arm 56 and media engaging member 80 may then be removed from media tester 10. A further support arm 56 and attached media engaging member 80 may then be secured to the adjustment member by fastener 62. In this manner, media tester 10 can be used to test a plurality of different required bend radii. In another exemplary approach, the support arm 56 may be permanently affixed, but a removable fastener may be used about the axis of rotation of drum 82 such that a first drum may be removed and a second drum added with a different radius r.

Adjustment member 50 is connected to test body 20 such that the adjustment member may rotate about test body 20. To rotate adjustment member 50 about the test body 20, stabilizer 59 may be disengaged from base surface 33 of axial groove 31 (e.g., by way of stabilizer screws 66). When using a stabilizer with stabilizer screws, once the stabilizer screws 66 are no longer in contact with base surface 33, adjustment member 50 may be rotated about the outer surface 30 of test body 20. Rotating the adjustment member 50 about the test body 20 also rotates the media engaging member 80 about the axis of the axial bore 32 of test body 20. When the desired position about the outer surface 30 of test body 20 has been reached, stabilizer 59 (e.g., screws 66) may be re-engaged against the base surface 33 of axial groove 31. When using a stabilizer with stabilizer screws, tightening the stabilizer screws 66 against the base surface 33 locks the adjustment member 50 to the test body 20, preventing further rotation of adjustment member 50.

A plurality of markers 86 may be disposed on the outer surface 30 of test body 20 at predetermined increments to indicate, for example, the number of degrees adjustment member 50 has rotated about test body 20, and thus how many degrees media engagement member 80 has rotated about the axis of axial bore 32. Markers 86 may include any suitable indicia to indicate the number of degrees that that adjustment member 50 has rotated about test body 20 from a reference point O. For example, markers 86 may be numbers indicating the degrees of rotation from reference point O along the outer surface 30 of the test body 20. Alternatively, markers 86 may be vertical lines spaced apart from each other, where the spacing between the vertical lines represents a specific number of degrees. After testing of a particular media 100 has been completed, adjustment member 50 may be rotated such that media engaging member 80 is aligned with reference point O.

Adjustment member 50 may also translate axially about test body 20. Disengaging stabilizers 59 from base surface 33 of axial groove 31 may also allow adjustment member 50 to be moved along the length of test body 20. Removing stabilizers 59 from the axial groove 31 will allow adjustment member 50 to axially translate along the length of test member 20. When adjustment member 50 is aligned with a further axial groove 31, adjustment member 50 may be reconnected to test member 20. When using stabilizer screws 66, stabilizers 59 may engage the test member 20 by tightening the stabilizer screws against the base surface 33 of axial groove 31, which prevents further axial movement of adjustment member 50. A plurality of axial markers 88 may also be disposed on the outer surface 30 of test body 20 to indicate the distance adjustment member 50 travels along test body 20, and thus the axial distance traveled by media engagement member 80.

As shown in FIG. 2, a plurality of guide members 92, 94 may be provided above the top surface 22 of test body 20, and a plurality of guide members 96, 98 may be provided below the bottom surface 26 of test body 20. Guide members 92, 94, 96, 98 may be pulleys that route or direct media 100 from one location to another (e.g., to a destination) while stabilizing media 100 to prevent the media from undesirably twisting. For example, guide members 92, 94 may route media 100 from a transmitter/receiver or transceiver 110 to media engaging member 80, and guide members 96, 98 may route media 100 from test body 20 to transmitter/receiver 110. Alternatively, a transmitter and a receiver may be provided separately. Guide members 92, 94, 96, 98 each may include a radius greater than or equal to the minimum bend radius of media 100 to prevent the media from experiencing bends that exceed the minimum bend radius of the media.

Weights 120, 122 may be connected to media 100 proximate the first and second ends 102, 104 of media 100. Weights 120, 122 may be heavy enough to place media 100 under tension to prevent media 100 from kinking or bending other than as desired for testing purposes. If weights 120, 122 are too heavy, damage may occur to media 100. If media 100 is kinked or bent during testing, media tester 10 may not be presented with a uniform cross-section of media 100 for testing. Further, placing media 202 under tension reduces the possibility of media 100 inadvertently including a bend that exceeds the minimum bend radius of the media.

Additionally, indicators 130, such as pieces of tape, may be affixed to media 100 in a plurality of locations along the length of media 100. In the illustrated approach, indicators 130 may be affixed to media 100 above and below media engaging member 80, and below test body 20. Indicators 130 are affixed to media 100 in the same orientation to indicate the orientation of media 100. If the orientation of any of indicators 130 changes, it can be determined that media 100 is being twisted. In this manner, indicators 130 can be used to ensure that media 100 is not being twisted while under test.

To test the required bend radius of media, first end 102 of media 100 is connected to transmitter/receiver 110 for transmitting a signal through media 100. Media 100 then passes about guide members 92, 94, which route media 100 to media engaging member 80. Media 100 is then coiled about the drum 82 of media engaging member 80, which includes a radius that generally corresponds to the required bend radius of media 100, such that media 100 experiences a bend equal to the radius of media engaging member 80. The power level of transmitted/receiver 110 may then be normalized to approximately zero.

Figure 3:
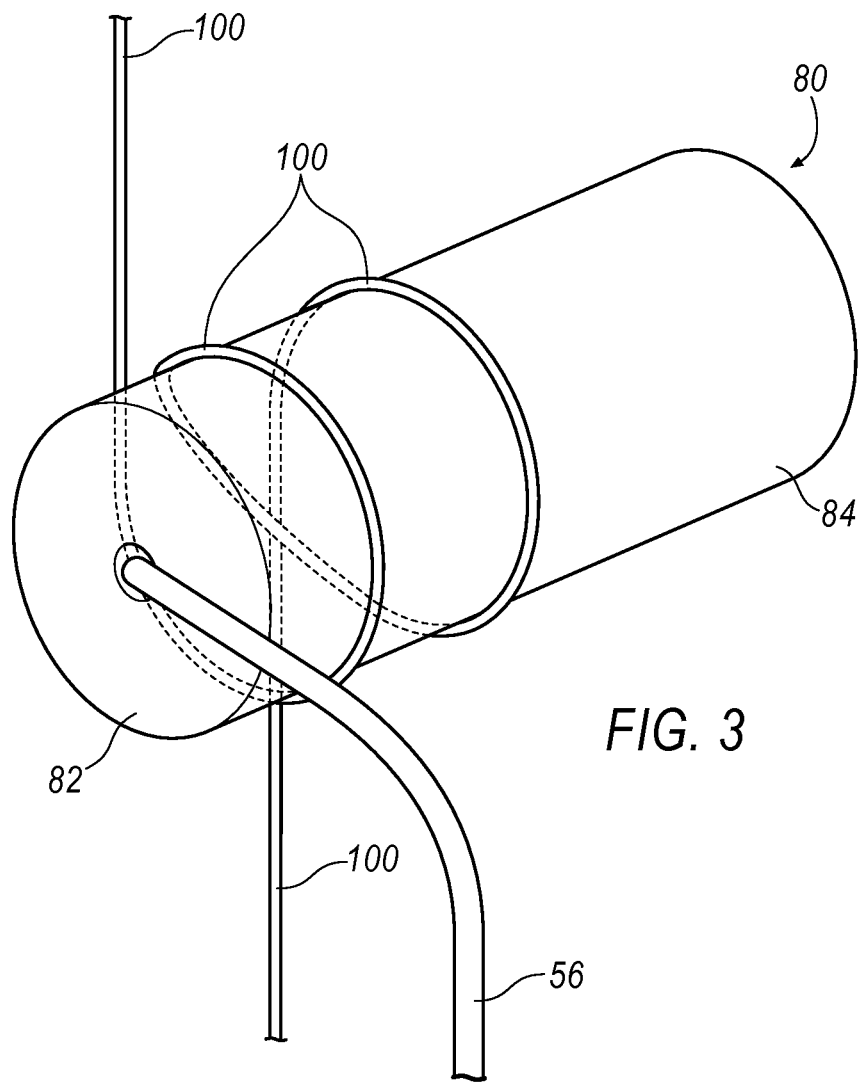
FIG. 3 is a perspective view of the media engagement member of the media tester of FIG. 1.

As shown in FIG. 3, media 100 may be coiled about drum 82 of media engaging member 80 more than once such that each coil of media 100 rests side by side one another about drum 82. Coils of media 100 should not overlap about drum 82 of media engaging member as such overlapping may affect the testing of media 100. In this manner, media 100 experiences multiple bends equal to the radius of media engaging member 80, and the multiple coils of media 100 may be tested simultaneously. In some exemplary approaches, track 84 may include a plurality of channels adjacent one another and extending about the circumference of track 84, each channel configured and sized to receive a single instance of media 100 to further minimize the likelihood of overlapping. When channels are used, however, the base of such a channel should correspond to the radius r.

Media 100 then passes through the axial bore 32 at the top surface 22 of test body 20 and travels through test body 20. Media 100 exits test body 20 through the bottom surface 26 and then passes about guide members 96, 98. The second end 104 of media 100 is also connected to transmitter/receiver 110 for receiving the transmitted signal.

In operation, transmitter/receiver 110 transmits a signal through the first end 102 of media 100, which then travels through media 100 about guide members 92, 94, around media engaging member 80, through test body 20, about guide members 96, 98 and back to transmitter/receiver 110, which measures whether the required bend radius of media 100 at this particular cross-section of media 100 has been exceeded. If the signal travels through media 100 to transmitter/receiver 110 without experiencing a signal loss, the required bend radius of media 100 has not been exceeded. The measurement may then be recorded. Transmitter/receiver 110 can also be used to test media 100 for polarization dependent loss.

Once the measurement has been made, media 100 is uncoiled from around media engaging member 80, and adjustment member 50 may be rotated about test body 20 to a desired axial angle. The rotation of adjustment member 50 also rotates support arm 56 and media engaging member 80, such that the drum 82 of media engaging member 80 is tangential to the axial direction of a different cross-section of media 100. Thus, the required bend radius of a different cross-section of media 100 can be tested. Media 100 is then recoiled about media engaging member 80, and a measurement is made for this particular cross-section of media 100. This may be repeated for cross-sections of media 100 at appropriate predetermined locations about the axis of media 100.

Additionally, after a measurement has been made and media 100 has been uncoiled from media engaging member 80, adjustment member 50 may be moved axially along test body 20 such that measurements may be made at different positions along the axial length of media 100.

Figure 4:
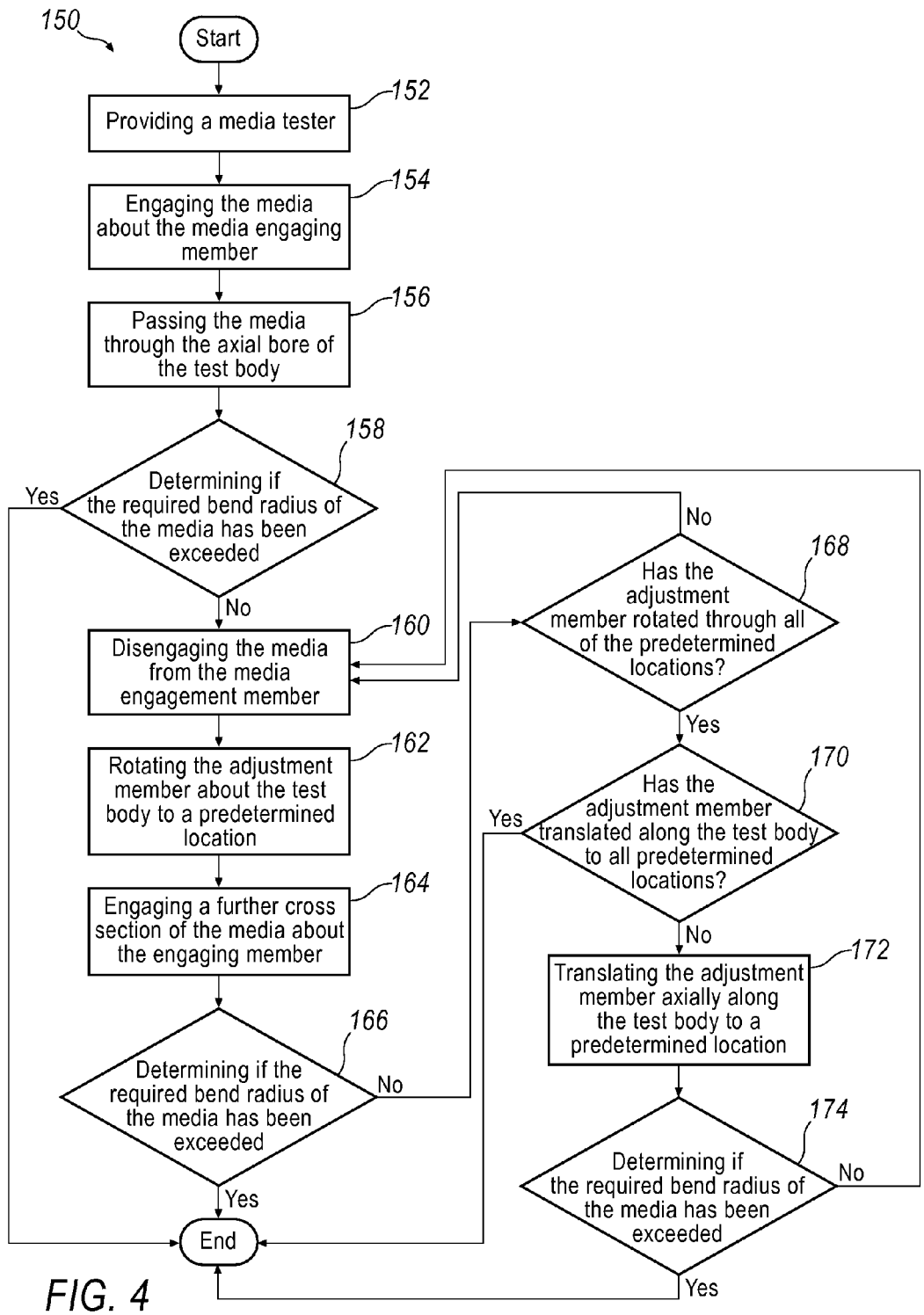
FIG. 4 illustrates an exemplary process for testing a required bend radius of media using the media tester of FIG. 1.

FIG. 4 illustrates an exemplary process 150 for testing the required bend radius of media 100.

Block 152 may include providing a media tester 10. The media tester 10 may include a test body 20 having an axial bore 32 configured to receive media 100 having a minimum bend radius, an adjustment member 50 connected to the test body 20, and a media engaging member 80 having a radius that generally corresponds to the required bend radius of media 100 connected to the adjustment member 50 and configured to receive media 100.

Block 154 may include engaging the media 100 about the media engaging member 80. For example, media 100 may be coiled about the media engaging member 80 once, or may be coiled about the media engaging member 80 a plurality of times.

Block 156 may include passing the media 100 through the axial bore 32 of the test body.

Decision point 158 may include determining if the required bend radius of the media 100 has been exceeded. For example, a signal may be transmitted from a transmitter/receiver 110 through a first end 102 of media 100 to a second end 104 of media 100, where the signal is received by transmitter/receiver 110. If the signal travels through media 100 to transmitter/receiver 110 without experiencing undue signal loss, the required bend radius of media 100 has not been exceeded. If the required bend radius has been exceeded, the process 150 may end. If the required bend radius has not been exceeded, the process 150 moves to block 160.

Block 160 may include disengaging the media 100 from the media engagement member 80.

Block 162 may include rotating the adjustment member 50 about the test body 20. For example, stabilizers 59 may be disengaged from the test body 20, which allows adjustment member 50 to rotate about the test body 20 such that media engaging member 80 is tangential to a further cross-section of media 100.

Block 164 may include engaging the further cross-section of media 100 about the media engaging member 80. For example, media 100 may be coiled about the media engaging member 80 once, or may be coiled about the media engaging member 80 a plurality of times.

Decision point 166 may include determining if the required bend radius of the media 100 has been exceeded. For example, a signal may be transmitted from a transmitter/receiver 110 through a first end 102 of media 100 to a second end 104 of media 100, where the signal is received by transmitter/receiver 110. If the signal travels through media 100 to transmitter/receiver 110 without experiencing a signal loss, the required bend radius of the further cross-section of media 100 has not been exceeded. If the required bend radius has been exceeded, the process 150 may end. If the required bend radius has not been exceeded, the process 150 moves to decision point 168.

Decision point 168 may include determining if the adjustment member 50 has rotated through all of the predetermined locations about the axis of media 100. If the adjustment member 50 has rotated through all predetermined locations, the process 150 moves to decision point 170. If the adjustment member 50 has not rotated through all the predetermined locations, the process 150 moves to block 160, and blocks 160 through 166 may be repeated.

Decision point 170 may include determining if the adjustment member 50 has translated to all predetermined locations along the axis of test body 20. If the adjustment member 50 has traveled to all predetermined locations along the axis of test body 20, the process 150 may stop. If the adjustment member 50 has not traveled to all predetermined locations along the axis of test body 20, the process moves to block 172.

Block 172 may include translating the adjustment member 50 along the axis of test body 20. For example, stabilizers 59 may be disengaged from the test body 20, which allows adjustment member 50 to be moved along the length of test body 20.

Decision block 174 may include determining if the required bend radius of the media 100 has been exceeded. If the required bend radius has been exceeded, the process 150 may end. If the required bend radius has not been exceeded, the process 150 moves to block 160, and blocks 160 through 166 may be repeated.

Another exemplary illustration of a media tester 200 is shown in FIGS. 5 through 9. Media tester 200 includes test body 220, adjustment member 250 connected to test body 220, and a media engaging member 280 connected to the adjustment member 250. Test body 220 may be a generally circular ring, having a first face 222 and a second opposing face 224 defining a bore 226 therethrough for receiving media 202 having a first end 204 and a second end 206. The plane of test body 220 is shown generally perpendicular to the longitudinal axis of media 202. A generally circular track 227 defined by outer track wall 228 and inner track wall 229 may be disposed on the first face 222 of test body 220.

Test body 220 may be mounted to a base 230 to stabilize test body 220 and to prevent test body 220 from moving during testing of media 202. A mounting arm 232 having a first end 234 and a second end 236 may be connected at the first end 234 to the second face 224 of test body 220. The second end 236 of mounting arm 232 may then be connected to a base mount 238, which in turn may be connected to base 230. In some approaches, it may be desirable for the base mount 238 to be able to move axially along base 230. Therefore, in the illustrated example, base mount 238 may be received in a base track 240 on base 230, such that base mount 238 may move axially along base 230, as discussed below. A plurality of axial markers 231 may also be disposed on base 230 to indicate the distance base mount 238 travels along base 230.

Figure 5:
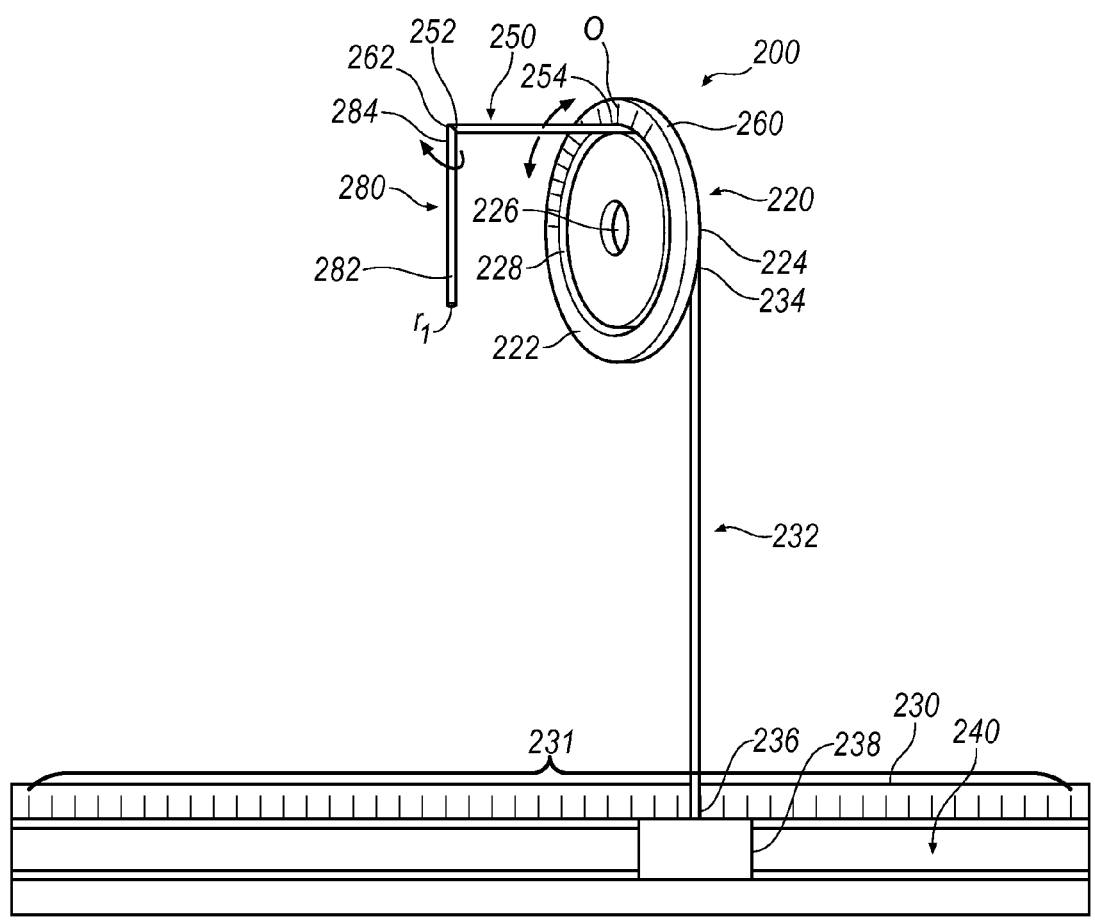
FIG. 5 is a perspective view of an alternate illustration of the media tester of FIG. 1.
Figure 6:
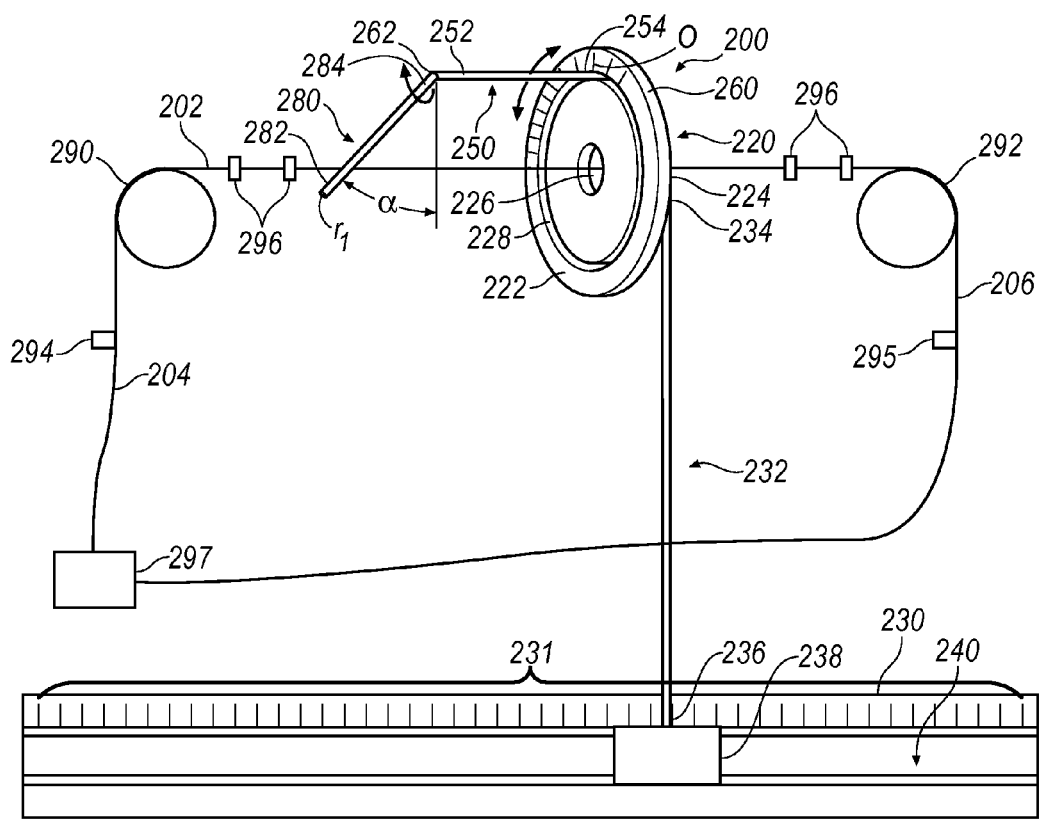
FIG. 6 is a further perspective view of the media tester of FIG. 5.
Figure 7:
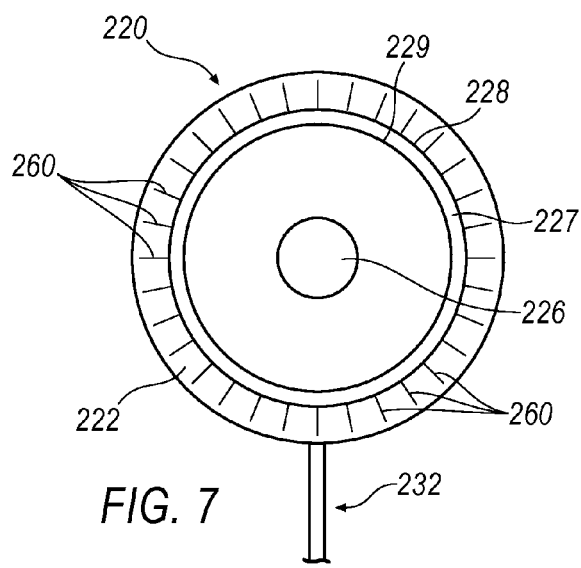
FIG. 7 is a planar view of the test body of the media tester of FIG. 5.
Figure 8:
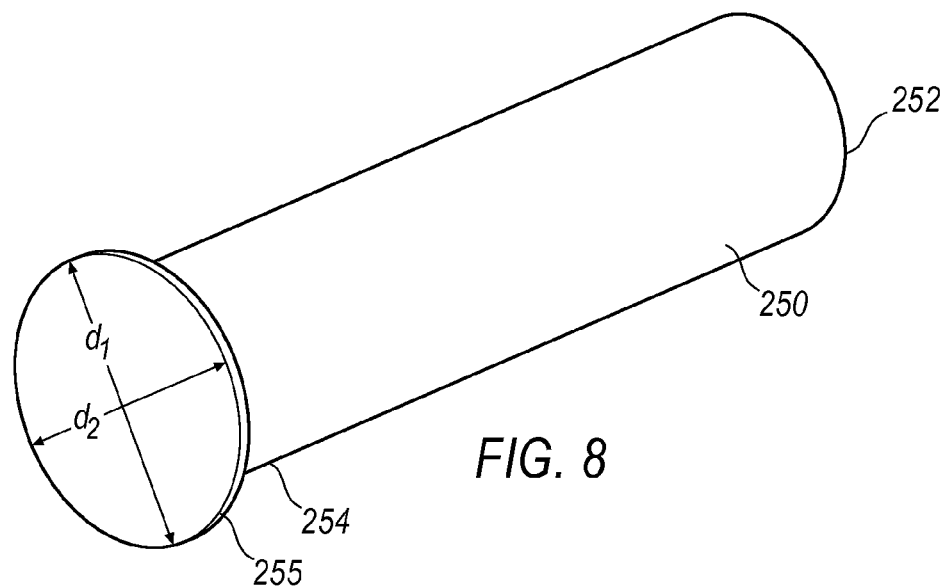
FIG. 8 is a perspective view of the adjustment member of the media tester of FIG. 5.

As seen in FIGS. 5 and 6, media tester 200 may also include an adjustment member 250 connected to test body 220 such that the adjustment member 250 may rotate about the bore 226 or test body 220. In the exemplary illustration, the adjustment member 250 is parallel to the axis of media 202 when media 202 passes through bore 226 of test body 220. Adjustment member 250 may include a bar having at least a generally circular cross section with a first end 252 and a second end 254. The second end 254 of adjustment member 250 may include an interlock 255, shown in FIG. 8, having a generally oval cross-section with a longer first diameter $d_1$ and a second shorter diameter $d_2$. Although interlock 255 is shown as having a generally oval cross-section, other configurations for interlock 255 may be used.

To secure the adjustment member 250 to the test body 220, the interlock 255 of adjustment member 250 may be inserted into track 227 such that the longer first diameter $d_1$ is generally tangential to track 227. After insertion, adjustment member 250 may be twisted or rotated about its axis. This causes interlock 255 to rotate within track 227, and the longer first diameter $d_1$ of interlock 255 to engage the outer and inner track walls 228, 229. The engagement of interlock 255 with outer and inner track walls 228, 229 locks adjustment member 250 in place, and prevents rotation of adjustment member 250 through track 227 about the bore 226. To rotate adjustment member 250 about track 227, adjustment member 250 may be twisted to release interlock 255 from engagement with track walls 228, 229. Adjustment member 250 may then moved along track 227 to a desired location. Adjustment member 250 may then be twisted again, to engage interlock 255 with the track walls 228, 229 to prevent further rotation of adjustment member 250 about the bore 226 of test body 220. Other suitable means for securing the adjustment member 250 to the test body may be used.

A plurality of markers 260 may be disposed on the first surface 222 of test body 220 along or proximate track 227 to indicate the number of degrees adjustment member 250 has rotated about the first face 22 of test body 220. Markers 260 may include any suitable indicia to indicate the number of degrees that that adjustment member 250 has rotated about the track 227 on test body 220 from a reference point O. For example, markers 260 may be numbers indicating the degrees of rotation from a starting point along track 227 of test body 220. Alternatively, markers 260 may be vertical lines spaced apart from each other, where the spacing between the vertical lines represents a specific number of degrees. After testing of a particular axial length of media 202 has been completed, adjustment member 250 may be rotated such that the adjustment member is aligned with the reference point O.

Media engaging member 280 may be connected to adjustment member 250 by a joint 262. Media engaging member 280 is connected to adjustment member 250 such that rotating adjustment member 250 about the bore 226 of test body 220 also rotates media engaging member 280 about the bore. Media engaging member 280 may be a tubular arm having a generally circular cross section including a first end 282 and a second end 284, the second end 284 of which may be connected to joint 262. Media engaging member 280 may be pivotally connected to joint 262 such that media engaging member 280 may rotate entirely about joint 262.

The radius $r_1$ of media engagement member 280 generally corresponds to the required bend radius of the media 202 being tested, such as the minimum bend radius of media 202. For example, if media 202 being tested has a minimum bend radius of 5 millimeters, the radius of media engaging member 280 is approximately 5 millimeters. Media 202 coiled about the media engagement member 280 will experience a bend that generally corresponds to the radius of media engagement member 280. This allows for the minimum bend radius of media 202 to be tested. Alternatively, media engaging member 80 may have a radius larger than the minimum bend radius of media 202 or a radius less than the minimum bend radius of media 202 to test the durability and performance of the media 202 at other required bend radii.

Media engaging member 280 may be replaced by a further media engaging member 280 having a different radius. To replace media engaging member 280, adjustment member 250 may be removed from engagement with track 227 by releasing interlock 255 from engagement with outer and inner track walls 228, 229. Adjustment member 250 and media engaging member 280 may then removed from media tester 200. A further adjustment member 250, with an attached media engaging member 280, may then be secured within track 227 by interlock 255. In this manner, media tester 200 can be used to test a plurality of different required bend radii.

As shown in FIG. 6, guide members 290, 292 may be provided on opposite sides of test body 220. Guide members 290, 292 may be pulleys which route or direct media 202 from one location to another while stabilizing media 202 to prevent media 202 from twisting. For example, guide member 290 may route media 202 from a transmitter/receiver or transceiver 297 to test body 220, and guide member 292 may route media 202 from guide member 292 to transmitter/receiver 297. Guide members 290, 292 each may include a radius greater than or equal to the minimum bend radius of media 202 to prevent the media from experiencing bends that exceed the minimum bend radius of the media.

Weights 294, 295 may be connected to media 202 proximate the first and second ends 204, 206 of media 202. Weights 294, 295 may be heavy enough to place media 202 under tension to prevent media 202 from kinking or bending other than as desired for testing purposes. If weight 294, 295 are too heavy, damage may occur to media 202. If media 202 is kinked or bent during testing, media tester 200 may not be presented with a uniform cross-section of media 202 for testing. Further, placing media 202 under tension reduces the possibility of media 202 inadvertently including a bend that exceeds the minimum bend radius of the media.

Additionally, indicators 296, such as pieces of tape, may be affixed to media 202 in a plurality of locations along the length of media 202. In the illustrated approach, indicators 296 may be affixed to media 202 in the same orientation to indicate the orientation of media 202. If the orientation of any of indicators 296 changes, it can be determined that media 202 is being twisted. In this manner, indicators 296 can be used to ensure that media 202 is not being twisted while under test.

To test a required bend radius of media 202, the first end 204 of media 202 is connected to transmitter/receiver 297 for transmitting a signal through media 202. Media 202 is then passed about guide member 290, through test body 220, and about guide member 292. The second end 206 of media 202 is connected to transmitter/receiver 297 for receiving the transmitted signal. The power level of transmitter/receiver 297 may then be normalized to approximately zero. Weight 294 is connected to media 202 proximate the first end 204 and weight 295 is connected to media 202 proximate the second end.

Figure 9:
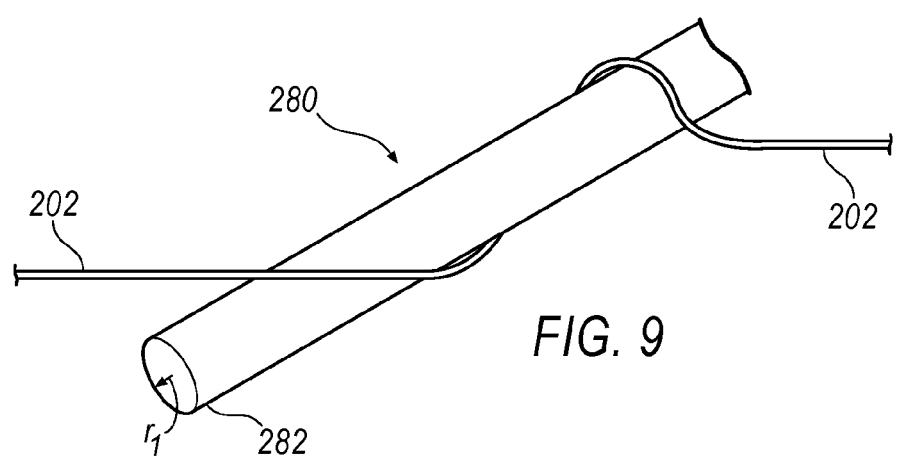
FIG. 9 is a perspective view of the media engaging member of the media tester of FIG. 6 after the media engaging member has engaged media.

Media engagement member 280 is then manually rotated about joint 262 into media 202 at an angle α such that the media engagement member catches and engages media 202. As media engagement member 280 is rotated about joint 262, media 202 is coiled around the circumference of media engagement member 280, such that media 202 experiences a bend that corresponds to the radius $r_1$ of media engagement member 280, as shown in FIG. 9. The tension in media 202 provided by weights 294, 295 prevents media 202 from slipping off of media engaging member 280.

Media engagement member 280 may be rotated into media 202 more than once, forming a coil of media 202 about media engagement member 280 for each complete rotation of media engagement member 280 about joint 262. Coils of media 202 are disposed along the length of media engagement member 280 such that the coils of media 202 do not overlap one another as such overlapping may affect the testing of media 202. In this manner, media 202 may experience multiple bends equal to the radius $r_1$ of media engagement member 280, such that multiple coils of media 202 may be tested simultaneously.

In operation, transmitter/receiver 297 transmits a signal through the first end 204 of media 202, which travels through media 202 about guide member 290, around media engaging member 280, about guide member 292, and back to transmitter/receiver 297, which measures whether the required bend radius of media 202 at this particular cross-section of media 202 has been exceeded. If the signal travels through media 202 to transmitter/receiver 297 without experiencing a signal loss, the required bend radius of media 202 has not been exceeded. After the measurement has been made and recorded, media engagement member 280 may be rotated in the opposite direction, uncoiling media 202 from media engagement member 280.

Adjustment member may then be rotated along track 227 to a different location along track 227, such that rotation of media engagement member 280 will contact a different cross-section of media 202. A measurement may then be made for a coil of media 202 experiencing a bend equal to the required bend radius of media 202 along this particular cross-section of media 202. This may be repeated for cross-sections of media 202 at predetermined locations about the axis of media 202.

Additionally, after a measurement has been made and media 202 has been uncoiled from media engagement member 280, base mount 238 may be moved axially along base track 240, which axially moves test body 220 along the axial direction of media 202. In this manner, measurements may be made at different positions along the length of media 202. Although media tester 200 is shown as being manually operated, media tester 200 may be automated.

With regard to the processes, systems, methods, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claimed invention.

It is to be understood that the above description is intended to be illustrative and not restrictive. Many embodiments and applications other than the examples provided would be apparent to those of skill in the art upon reading the above description. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future embodiments. In sum, it should be understood that the invention is capable of modification and variation and is limited only by the following claims.

All terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary.

What is claimed is:

1. A media tester, comprising:
    a generally cylindrical test body having an axial bore between a first face and a second face thereof along an axis thereof, the axial bore being configured to receive media having a minimum bend radius;
    an adjustment member; and
    a media engaging member connected to the adjustment member, the media engaging member being configured to engage the media received by the axial bore,
    wherein the test body includes at least one guide structure encircling the axial bore by which the adjustment member is selectively secured to the test body and which is configured to allow for rotation of the adjustment member about the axis of the test body.

2. The media tester of claim 1, wherein:
    the media engaging member is generally cylindrical with a radius r and is configured to perform a testing operation such that during the testing operation the media received by the media engaging member is bent by the media engaging member to the radius r, and
    the media tester is configured such that the radius r is the smallest radius to which the media is bent while within the media tester.

3. The media tester of claim 2, wherein the adjustment member includes an arm portion that extends generally parallel to the axis of the test body and is connected to the media engaging member such that during the testing operation an axis of the media engaging member is transverse to the axis of the test body and a circumferential surface of the media engaging member is substantially tangent to the axis of the test body.

4. The media tester of claim 2, wherein the media tester is configured such that rotating the adjustment member about the axis of the test body changes a plane of the media that will be bent by the media engaging member during the testing operation.

5. The media tester of claim 1, wherein the at least one guide structure comprises a circumferential groove in an outer circumferential surface of the test body.

6. The media tester of claim 5, wherein the adjustment member comprises:
a ring portion that is configured to encircle the circumferential surface of the test body,
stabilizers connected to the ring portion and configured to selectively secure the adjustment member to the test body via the at least one guide structure, and
an arm portion that extends generally parallel to the axis of the test body and is connected to the ring portion and to the media engaging member.

7. The media tester of claim 1, wherein the at least one guide structure comprises a generally circular track disposed in the first face of the test body.

8. The media tester of claim 7, wherein the adjustment member comprises an arm portion that extends generally parallel to the axis of the test body and is connected to the media engaging member, the arm portion being configured to selectively secure the adjustment member to the test body via the at least one guide structure.

9. The media tester of claim 8,
wherein the media engaging member is connected to the arm portion of the adjustment member such that the media engaging member can rotate with respect to the arm portion of the adjustment member.

10. The media tester of claim 7, wherein the test body is connected to a base via a mounting arm such that a position of the test body relative to the base may be changed in a direction parallel to the axis of the test body.

11. A media tester, comprising:
a generally cylindrical test body having an axial bore between a first face and a second face thereof along an axis thereof, the axial bore being configured to receive media having a minimum bend radius;
a media engaging member configured to engage the media received by the axial bore and to perform a testing operation that includes bending the media to a radius r; and
an adjustment member that includes an arm portion that extends generally parallel to the axis of the test body and is connected to the media engaging member such that during performance of the testing operation a longitudinal axis of the media engaging member is transverse to an axis of the test body and a circumferential surface of the media engaging member is substantially tangential to the axis of the test body,
wherein the adjustment member is selectively secured to the test body by at least one guide structure, which is configured to allow for rotation of the arm portion of the adjustment member about the axis of the test body.

12. The media tester of claim 11, wherein the adjustment member further comprises:
a ring portion that is configured to encircle the circumferential surface of the test body and is connected to the arm portion, and
stabilizers connected to the ring portion and configured to selectively secure the adjustment member to the test body via the at least one guide structure.

13. The media tester of claim 12, wherein the at least one guide structure comprises a circumferential groove in an outer circumferential surface of the test body.

14. The media tester of claim 11, wherein the adjustment member includes an interlock disposed on an end of the arm portion, the interlock being configured such that when the interlock is inserted into the at least one guide structure and rotated about an axis of the arm portion the interlock engages the at least one guide structure in a manner that fixedly secures the adjustment member to the test body.

15. The media tester of claim 14, wherein the at least one guide structure comprises a generally circular track disposed in the first face of the test body.

16. The media tester of claim 15, wherein:
the media engaging member is generally cylindrical with a radius r, and
the media tester is configured such that the radius r is the smallest radius to which the media is bent while the media is within the media tester.

17. A method of testing media, comprising:
providing a media tester comprising a generally cylindrical test body having an axial bore between a first face and a second face thereof along an axis thereof, the axial bore being configured to receive media having a minimum bend radius, an adjustment member, and a media engaging member connected to the adjustment member, the media engaging member being configured to receive the media, wherein the test body includes at least one guide structure encircling the axial bore by which the adjustment member is selectively secured to the test body and which is configured to allow for rotation of the adjustment member about the axis of the test body;
securing the adjustment member to the test body via the at least one guide structure such that a reference point on the adjustment member is at a first position;
passing the media through the axial bore of the test body; and
performing a testing operation comprising:
engaging the media about the media engaging member;
bending the media via the media engaging member to a bend radius r; and
determining if the bend in the media caused by the media engaging member exceeds the minimum bending radius of the media.

18. The method of testing media of claim 17, further comprising:
disengaging the media from the media engaging member;
loosening the adjustment member in the at least one guide structure such that the adjustment member is rotatable about the axis of the test body;
rotating the adjustment member about the axis of the test body and securing the adjustment member such that the reference point on the adjustment member is at a second position; and
again performing the testing operation.

19. The method of testing media of claim 18, wherein rotating the adjustment member about the axis of the test body changes a plane of the media that is bent by the media engaging member.

20. The method of testing media of claim 17, further comprising:
disengaging the media from the media engaging member;

moving the adjustment member relative to the media in a direction parallel to the axis of the test body, including one of:
keeping the test body and the adjustment member fixed with respect to each other as the adjustment member is moved relative to the media, and
loosening the adjustment member in the at least one guide structure, moving the adjustment member relative to the test body as the adjustment member is moved relative to the media, and securing the adjustment member to the test body; and
again performing the testing operation.

21. The method of testing media of claim 17, further comprising performing the testing operation for a plurality of different bending planes of the media by rotating the adjustment member about the axis of the test body between performances of the testing operation.

22. The method of testing media of claim 17, further comprising performing the testing operation for a plurality of different cross sections of the media by, between performances of the testing operation, moving the adjustment member relative to the media in a direction parallel to the axis of the test body, including one of:
keeping the test body and the adjustment member fixed with respect to each other as the adjustment member is moved relative to the media, and
moving the adjustment member relative to the test body as the adjustment member is moved relative to the media.

\* \* \* \* \*